(12) United States Patent
Foody et al.

(10) Patent No.: US 10,513,714 B2
(45) Date of Patent: *Dec. 24, 2019

(54) LIGNOCELLULOSIC CONVERSION PROCESS COMPRISING SULFUR DIOXIDE AND/OR SULFUROUS ACID PRETREATMENT

(71) Applicant: Iogen Corporation, Ottawa (CA)

(72) Inventors: Brian Foody, Ottawa (CA); Jeffrey S. Tolan, Ottawa (CA)

(73) Assignee: IOGEN CORPORATION, Ottawa, ON (CA)

( * ) Notice: Subject to any disclaimer, the term of this patent is extended or adjusted under 35 U.S.C. 154(b) by 86 days.

This patent is subject to a terminal disclaimer.

(21) Appl. No.: 15/550,515

(22) PCT Filed: Mar. 16, 2016

(86) PCT No.: PCT/CA2016/050289
§ 371 (c)(1),
(2) Date: Aug. 11, 2017

(87) PCT Pub. No.: WO2016/145528
PCT Pub. Date: Sep. 22, 2016

(65) Prior Publication Data
US 2019/0106718 A1    Apr. 11, 2019

Related U.S. Application Data

(60) Provisional application No. 62/232,151, filed on Sep. 24, 2015, provisional application No. 62/133,609, filed on Mar. 16, 2015.

(51) Int. Cl.
| | |
|---|---|
| *C12P 19/02* | (2006.01) |
| *C12P 7/10* | (2006.01) |
| *C01C 1/24* | (2006.01) |
| *C05C 3/00* | (2006.01) |
| *C05D 1/02* | (2006.01) |
| *C08H 8/00* | (2010.01) |
| *C12P 19/14* | (2006.01) |
| *C10L 1/02* | (2006.01) |
| *C05F 17/00* | (2006.01) |
| *C01D 5/00* | (2006.01) |

(Continued)

(52) U.S. Cl.
CPC ................. *C12P 7/10* (2013.01); *C01C 1/24* (2013.01); *C01D 5/00* (2013.01); *C01D 5/04* (2013.01); *C05C 3/00* (2013.01); *C05D 1/02* (2013.01); *C05F 17/0045* (2013.01); *C07G 1/00* (2013.01); *C08H 8/00* (2013.01); *C10L 1/02* (2013.01); *C12F 3/00* (2013.01); *C12P 5/023* (2013.01); *C12P 7/16* (2013.01); *C12P 7/22* (2013.01); *C12P 19/02* (2013.01); *C12P 19/14* (2013.01); *C01C 1/164* (2013.01); *C12P 2201/00* (2013.01); *C12P 2203/00* (2013.01); *Y02E 50/10* (2013.01); *Y02E 50/16* (2013.01); *Y02E 50/343* (2013.01); *Y02P 20/145* (2015.11); *Y02W 30/43* (2015.05); *Y02W 30/47* (2015.05)

(58) Field of Classification Search
CPC ..... C12P 7/10; C12P 2201/00; C12P 2203/00; C12P 7/16; C12P 5/023; C10L 2200/0469; Y02E 50/16; Y02E 50/10; Y02E 50/343; C07G 1/00; C08H 8/00; C12F 3/00; D21C 11/0057; D21C 11/14; D21C 3/003; D21C 3/02; D21C 3/222; Y02P 20/145; Y02W 30/47; C13K 1/02
See application file for complete search history.

(56) References Cited

U.S. PATENT DOCUMENTS

| | | |
|---|---|---|
| 2,418,167 A | 4/1947 | Du Bois |
| 3,562,319 A | 2/1971 | Brink |
| (Continued) | | |

FOREIGN PATENT DOCUMENTS

| | | |
|---|---|---|
| GB | 2033366 A | 5/1990 |
| WO | 2006/032282 A1 | 3/2006 |
| (Continued) | | |

OTHER PUBLICATIONS

Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.

(Continued)

*Primary Examiner* — Lynn Y Fan
(74) *Attorney, Agent, or Firm* — Knobbe Martens Olson & Bear LLP

(57) ABSTRACT

Provided herein is a process for producing one or more products from a lignocellulosic feedstock. The process comprises treating the lignocellulosic feedstock by contacting the feedstock at least sulfur dioxide, sulfurous acid, or a combination thereof to produce a pretreated feedstock comprising one or more sulfonic acids. A process stream comprising one or more sulfonic acids is subsequently treated in a wet oxidation step to produce a stream comprising at least soluble oxidized phenolic compounds. The soluble oxidized phenolic compounds are then fed to an anaerobic digestion to produce methane. Optionally, hydrogen sulfide is produced during the anaerobic digestion. The hydrogen sulfide may then be converted to an acid selected from sulfur dioxide, sulfurous acid or a combination thereof in one or more steps. The acid may then be re-used in treatment as desired.

13 Claims, 1 Drawing Sheet

(51) Int. Cl.
| | |
|---|---|
| *C01D 5/04* | (2006.01) |
| *C07G 1/00* | (2011.01) |
| *C12P 7/16* | (2006.01) |
| *C12F 3/00* | (2006.01) |
| *C12P 5/02* | (2006.01) |
| *C12P 7/22* | (2006.01) |
| *C01C 1/16* | (2006.01) |

(56) References Cited

U.S. PATENT DOCUMENTS

| | | |
|---|---|---|
| 4,384,897 A | 5/1983 | Brink |
| 5,221,357 A | 6/1993 | Brink |
| 5,789,210 A | 8/1998 | Ho et al. |
| 5,866,382 A | 2/1999 | Hallborn et al. |
| 6,423,236 B1 | 7/2002 | Shiota et al. |
| 6,475,768 B1 | 11/2002 | Otero et al. |
| 6,582,944 B1 | 6/2003 | Hallborn et al. |
| 7,527,927 B1 | 5/2009 | Ho et al. |
| 7,527,951 B2 | 5/2009 | Londesborough et al. |
| 7,585,652 B2 | 9/2009 | Foody et al. |
| 7,622,284 B2 | 11/2009 | Op Den Camp et al. |
| 7,754,456 B2 | 7/2010 | Penttila et al. |
| 8,038,842 B2 | 10/2011 | Retsina et al. |
| 8,247,203 B2 | 8/2012 | Foody et al. |
| 8,268,125 B2 | 9/2012 | Retsina et al. |
| 8,409,836 B2 | 4/2013 | Vehmaanpera et al. |
| 8,506,716 B2 | 8/2013 | Ahring et al. |
| 8,709,770 B2 | 4/2014 | Harlick et al. |
| 8,728,243 B2 | 4/2014 | van der Meulen et al. |
| 8,815,499 B2 | 4/2014 | Alriksson et al. |
| 8,834,633 B2 | 9/2014 | van der Meulen et al. |
| 8,871,475 B2 | 10/2014 | Alriksson et al. |
| 8,911,979 B2 | 12/2014 | Foody et al. |
| 9,012,188 B2 | 4/2015 | Van Heiningen et al. |
| 9,090,915 B2 | 7/2015 | Wang et al. |
| 9,102,951 B2 | 8/2015 | Griffin et al. |
| 9,290,821 B2 | 3/2016 | Blackbourn et al. |
| 9,574,212 B2 | 2/2017 | Foody et al. |
| 2007/0254348 A1* | 11/2007 | Retsina .................. C13K 1/02 435/161 |
| 2009/0118477 A1 | 5/2009 | Hallberg et al. |
| 2010/0056774 A1 | 3/2010 | Anand et al. |
| 2010/0279361 A1 | 11/2010 | South et al. |
| 2011/0039318 A1 | 2/2011 | Lehr |
| 2011/0300586 A1 | 12/2011 | Liu et al. |
| 2012/0041186 A1 | 2/2012 | Pschorn et al. |
| 2012/0052534 A1 | 3/2012 | Harlick et al. |
| 2012/0073199 A1* | 3/2012 | Lewis .................. C10B 53/02 48/127.5 |
| 2012/0237983 A1 | 9/2012 | Harlick |
| 2013/0071903 A1 | 3/2013 | Rowland et al. |
| 2014/0034047 A1 | 2/2014 | Retsina et al. |
| 2014/0053827 A1 | 2/2014 | Baudel et al. |
| 2014/0054506 A1 | 2/2014 | Melin et al. |
| 2014/0142351 A1 | 5/2014 | Johnston et al. |
| 2014/0154746 A1 | 6/2014 | Jonsson et al. |
| 2014/0163210 A1 | 6/2014 | Retsina et al. |
| 2014/0178944 A1 | 6/2014 | Parekh et al. |
| 2014/0182582 A1 | 7/2014 | Retsina et al. |
| 2014/0186899 A1 | 7/2014 | Retsina et al. |
| 2014/0186903 A1 | 7/2014 | Retsina et al. |
| 2014/0199740 A1 | 7/2014 | Merrill et al. |
| 2015/0050707 A1 | 2/2015 | Gapes et al. |
| 2015/0259709 A1 | 9/2015 | Retsina et al. |

FOREIGN PATENT DOCUMENTS

| | | |
|---|---|---|
| WO | 2006/034590 A1 | 4/2006 |
| WO | 2006/034591 A1 | 4/2006 |
| WO | 2006/128304 A1 | 12/2006 |
| WO | 2008/041840 A1 | 4/2008 |
| WO | 2010/022511 A1 | 3/2010 |
| WO | 2011/080131 A2 | 7/2011 |
| WO | 2012/117161 A1 | 9/2012 |
| WO | 2013/113579 A1 | 8/2013 |
| WO | 2014/106222 A2 | 7/2014 |
| WO | 2014/113615 A1 | 7/2014 |
| WO | 2016/145527 A1 | 9/2016 |
| WO | 2016/145529 A1 | 9/2016 |
| WO | 2016/145530 A1 | 9/2016 |
| WO | 2016/145531 A1 | 9/2016 |

OTHER PUBLICATIONS

Schell et al., "Pretreatment of Softwood by Acid-Catalyzed Steam Explosion Followed by Alkali Extraction," 1998, Applied Biochemistry and Biotechnology, pp. 17-24, vol. 70-72.

Schwald et al., "Assessment of Pretreatment Conditions to Obtain Fast Complete Hydrolysis on High Substrate Concentrations," 1989, Applied Biochemistry and Biotechnology, pp. 29-44, vol. 21/21.

Sendelius et al., "Steam Pretreatment Optimisation for Sugarcane Bagasse in Bioethanol Production," 2005, Master of Science Thesis, Lund University, Sweden.

International Preliminary Report on Patentability dated Sep. 19, 2017 for PCT Application No. PCT/CA2016/050289, filed Mar. 16, 2016.

Shevchenko et al., "Optimization of monosaccharide recovery by post-hydrolysis of the water-soluble hemicellulose component after steam explosion of softwood chips," 2000, Bioresource Technology, pp. 207-211, vol. 72.

Shevchenko et al., "The Nature of Lignin from Steam Explosion/ Enzymatic Hydrolysis of Softwood," 1999, Applied Biochemistry and Biotechnology, pp. 867-876, vol. 77-79.

Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.

Shuai et al., "Cornparitive study of SPORL and dilute-acid pretreatments of spruce for cellulosic ethanol production," 2010, Bioresource Technology, pp. 3106-3114, vol. 2010.

Sipos et al., "Steam pretreatment of dry and ensiled industrial hemp for ethanol production," 2010, Biomass and Bioenergy, pp. 1-11.

Soderstrom et al. "Effect of Washing on Yield in One- and Two-Step Steam Pretreatment of Softwood for Production of Ethanol," 2004, Biotehncol. Prog., pp. 744-749, vol. 20.

Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.

Soderstrom et al. "Two-Step Steam Pretreatment of Softwood with SO2 impregnation for Ethanol Production," 2002, Applied Biochemistry and Biotechnology, pp. 5-21, vol. 98-100.

Szengyel et al., "Cellulase Production of Trichoderma reesei Rut C 30 Using Steam-Penetrated Spruce," 2000, Applied Biochemistry and Biotechnology, pp. 679-691, vol. 84-86.

Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

Tengborg et al., "Reduced inhibition of enzymatic hydrolysis of steam-pretreated softwood," 2001, Enzyme and Microbial Technology, pp. 835-844, vol. 28.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.

Trajano et al. "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergetic effects of mixing hybrid poplar and wheat straw biomass for bioconversion processes," 2015, Biotechnol Biofuels, pp. 1-10, vol. 8:226.

(56) References Cited

OTHER PUBLICATIONS

Von Sivers et al., "A Techno-Economical Comparison of Three Processes for the Production of Ethanol from Pine," 1995, Bioresource Technology, pp. 43-52, vol. 51.
Wang et al., "Lignosulfonate and elevated pH can enhance enzymatic saccharification of lignocelluloses," 2013, Biotechnology for Biofuels, pp. 1-10, vol. 6:9.
Wang et al., "Ethanol production from poplar wood through enzymatic saccharification and fermentation by dilute acid and SPORL pretreatrnents," 2012, Fuel, pp. 606-614, vol. 95.
Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.
Wayman et al., "Hydrolysis of Biomass by Sulphur Dioxide," 1984, Biomass, pp. 183-191, vol. 6.
Wayman et al., "SO2 Catalysed Prehydrolysis of Coniferous Wood for Ethanol Production," 1986, Biotechnology Letters, pp. 749-752, vol. 8, No. 10.
Wiman et al., "Cellulose accessibility determines the rate of enzymatic hydrolysis of steam-pretreated spruce," 2012, Bioresource Technology, pp. 208-215, vol. 126.
Wolfinger et al., "Modeling of the Acid Sulfite Pulping Process.— Problem Definition and Theoretical Approach for a solution with the Main Focus on the Recovery of Cooking Chemicals," 2004, Lenzinger Berichte, pp. 35-45, vol. 83.
Wooley, Bob, "Production of 1,000 Gallons of BioJet," 2015, Presentation from 2015 Annual Meeting of Northwest Advanced Renewables Alliance (NARA).
Wyman et al., "Comparative data on effects of leading pretreatments and enzyme loadings and formulations on sugar yields from different switchgrass sources," 2011, Bioresource Technology, 11052-11062, vol. 102.
Wyman et al., "Comparitive Sugar Recovery and Fermentation Data Following Pretreatment of Poplar Wood by Leading Technologies," 2009, Biotechnol. Prog., pp. 333-339, vol. 25, No. 2.
Fan et al., "Optimization of SO2-catalyzed hydrolysis of corncob for xylose and xylitol production," 2014, J Chem Technol Biotechnol, pp. 1720-1726, vol. 89.
Zhang et al., "Sulfite (SPORL) pretreatment of switchgrass for enzymatic saccharification," 2013, Bioresource Technology, pp. 127-134, vol. 129.
Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.
Zhu et al., "Woody biomass pretreatment for cellulosic ethanol production: Technology and energy consumption evaluation," 2010, Bioresource Technology, pp. 4992-5002, vol. 101.
Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.
Zhu et al., "Ethanol production from SPORL-pretreated lodgepole pine: preliminary evaluation of mass balance and process energy efficiency," 2010, Appl Microbiol Biotechnol, pp. 1355-1365, vol. 86.
Zhu et al., "High Titer Ethanol Production from Forest Residue Using Sulfite Mill Pulping Chemistry," 2015, Presentation at 2015 TAPPI IBBC.
Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.
Zhu et al., "On Polydispersity of Plant Biomass Recalcitrance and its Effects on Pretreatment Optimization for Sugar Production," 2011, Bioenerg. Res., pp. 201-210, vol. 4.
Zhu et al., Quantitative predictions of bioconversion of aspen by dilute acid and SPORL pretreatments using a unified combined hydrolysis factor (CHF), 2012, Process Biochemistry, pp. 785-791, vol. 47.
Zhu et al., "Sulfite pretreatment (SPORL) for robust enzymatic saccharification of spruce and red pine," 2009, Bioresource Technology, pp. 2411-2418, vol. 100.
Barakat et al., "Effect of lignin-derived and furan compounds found in lignocellulosic hydrolysates on biomethane production", Bioresource Technology, 2012, vol. 104, pp. 90-99.
Taherzadeh and Karimi, "Pretreatment of Lignocellulosic Wastes to Improve Ethanol and Biogas Production: A review". Int. J. Mol. Sci., 2008, vol. 9, No. 9, pp. 1621-1651,
Monlau et al., "Lianocellulosic Materials into Biohydrogen and Biomethane: Impact of Structural Features and Pretreatment", Critical Reviews in Environmental Science and Technology, 2013, vol. 43, No. 3, pp. 260-322.
Matsakas et al., "Sequential Parametric Optimization of Methane Production from Different Sources of Forest Raw Material", Front. Microbiol., 2015, vol. 6, Article 1163.
Cavka et al., "Ozone Detoxification of Steam-Pretreated Norway Spruce", Biotechnol. Biofuels, 2015, vol. 8, p. 196.
Nguyen et al., "Two-Stage Dilute Acid Pretreatment of Softwoods," 2000, Applied Biochemistry and Biotechnology, 561-576, vol. 84-86.
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 19-145, vol. 44.
Ramos et al. "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 821-831, vol. 15.
Sassner et al., "Steam Pretreatment of Salix with and without SO2 Impregnation for Production of Bioethanol," 2005, Applied Biochemistry and Biotechnology, pp. 1101-1117, vol. 121-124.
Bensah, E. and Mensah, M., "Chemical Pretreatment Methods for the Production of Cellulosic Ethanol: Technologies and Innovations," International Journal of Chemical Engineering, 2013, pp. 1-21, vol. 2013.
Bhalla, A. et al., "Improved lignocellulose conversion to biofuels with thermophilic bacteria and thermostable enzymes," Bioresource Technology, 2013, pp. 751-759, vol. 128.
Boussaid, A., et al., "Fermentability of the Hemicellulose-Derived Sugars from Steam-Exploded Softwood (Douglas Fir),", Biotechnology and Bioengineering, 1999, pp. 284-289, vol. 64, No. 3.
Brownell, H. and Saddler, J., "Steam Pretreatment of Lignocellulosic Material for Enhanced Enzymatic Hydrolysis," Biotechnology and Bioengineering, 1987, pp. 228-235, vol. 29.
Bura, et al., "Moving towards commercialization of lignocellulosic biomass to fuels to chemicals. How to deal with heterogeneous biomass?" University of Washington Biofuels and Bioproducts Laboratory, 2012.
Bura, R., et al., "Influence of Xylan on the Enzymatic Hydrolysis of Steam-Pretreated Corn Stover and Hybrid Poplar," Biotechnol Prog, 2009, pp. 315-322, vol. 25, No. 2.
Bura, R., et al., "SO2-Catalyzed Steam Explosion of Corn Fiber for Ethanol Production", Applied Biochemistry and Biotechnology, 2002, pp. 59-72, vols. 98-100.

(56) References Cited

OTHER PUBLICATIONS

Carrasco, C., et al., "SO2-catalysed steam pretreatment of quinoa stalks," J Chem Technol Biotechnol, 2015, pp. 64-71, vol. 90.
Carrasco, C., et al., "SO2-catalyzed steam pretreatment and fermentation of enzymatically hydrolyzed sugarcane bagasse," Enzyme and Microbial Technology, 2010, pp. 64-73, vol. 46.
Carrasco, C., "Arabinosylated phenolics obtained from SO2-steam-pretreated sugarcane bagasse," Journal of Chemical Technology and Biotechnology, 2012, pp. 1723-1726, vol. 87.
Chacha, N., et al., "Steam Pretreatment of Pine (*Pinus patula*) Wood Residue for the Production of Reducing Sugars," Cellulose Chemistry and Technology, 2011, pp. 495-501, vol. 45 (7-8).
Chandra, R., et al., "Enhancing Hemicellulose Recovery and the Enzymatic Hydrolysis of Cellulose by Adding Lignosulfonates during the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Clark, T.A. et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark, T.A. et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of CO2 and SO2," Biotechnology for Biofuels, 2012, pp. 1-8, vol. 5:36.
De Bari et al., "SO2-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (*Eucalyptus regnans*) and Softwood (*Pinus radiata*) Sawdust for the Production of Cellulolytic Enzymes and Fermentable Substrates," Biocatalysis, 1987, pp. 63-75, vol. 1.
Ehsanipour, Mandana "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of SO2 arid H2SO4 Impregnation of Willow Prior to Steam Pretreatment," 1995, Bioresource Engineering, pp. 225-229, vol. 52.
Elander, et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Galbe et al., "A review of the production of ethanol from softwood," 2002, Appl Microbial Biotechnol, pp. 618-628, vol. 59.
Garlock et al., "Comparative material balances around pretreatment technologies for the conversion of switchgrass to soluble sugars," 2011, Bioresource Technology, pp. 11063-11071, vol. 102.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High SO2 Loading at Low Temperature," 2016, Industrial Biotechnology, pp. 168-175, vol. 12, No. 3.
Hodge et al., "Soluble and insoluble solids contributions to high-solids enzymatic hydrolysis of lignocellulose," 2006, Bioresource Technology, pp. 8940-8948, vol. 99.
Hodge et al., "Soluble and insoluble solids contributions to high-solids enzymatic hydrolysis of lignocellulose," 2008, Bioresource Technology, pp. 8940-8948, vol. 99.
Kumar et al., "Access of Cellulase to Cellulose and Lignin for Poplar Solids Produced by Leading Pretreatment Technologies," 2009, Biotechnol. Prog., pp. 807-819, vol. 25, No. 3.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Effect of Sulfite Pretreatment to Overcome the Recalcitrance of Lignin (SPORL) on Enzymatic Saccharification of Corn Stalk," 2011, Bioresouces, 5001-5011, vol. 6(4).
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37.
Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Monavari et al., "Improved One-Step Steam Pretreatment if SO2-Impregnated Softwood with Time-Dependant Temperature Profile for Ethanol Production," 2010, Biotechnol. Prog., pp. 1054-1060, vol. 26, No. 4.
Nguyen et al., "Dilute Acid Pretreatment of Softwoods," 1998, Applied Biochemistry and Biotechnology, pp. 77-89, vol. 70-72.
Kumar et al., Effects of Cellulase and Xylanase Enzymes on the Deconstruction of Solids from Pretreatment of Poplar by LeadingTechnologies, Biotechnol. Prag., vol. 25, No. 2, (2009) pp. 302-314.
Felby et al., "Ethanol from Wheat Straw Cellulose by Wet Oxidation Pretreatment and Simultaneous Saccharifcation and Fermentation," American Chemical Society, ACS Symposium Series, 2003, pp. 157-174.

\* cited by examiner

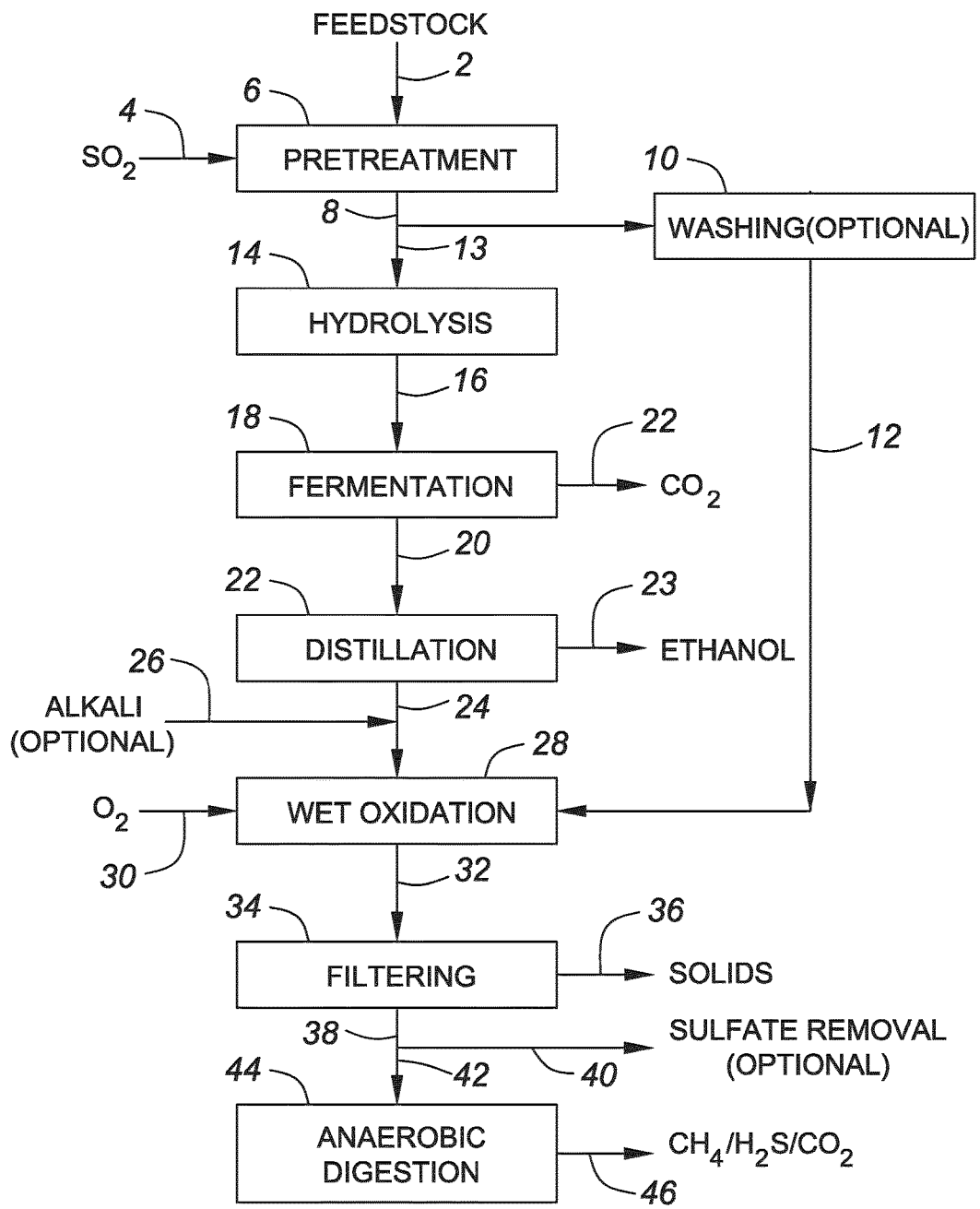

LIGNOCELLULOSIC CONVERSION PROCESS COMPRISING SULFUR DIOXIDE AND/OR SULFUROUS ACID PRETREATMENT

CROSS-REFERENCE TO RELATED APPLICATIONS

This application is a national stage application of PCT/CA2016/050289 having an international filing date of Mar. 16, 2016, which claims the priority benefit of provisional application No. 62/133,609, filed Mar. 16, 2015, and provisional application No. 62/232,151, filed Sep. 24, 2015, each of which is incorporated herein by reference.

TECHNICAL FIELD

The present invention relates to a process for treating lignocellulosic feedstock and in particular relates to a lignocellulosic conversion process comprising sulfur dioxide and/or sulfurous acid treatment, and a wet oxidation.

BACKGROUND

The production of fuel ethanol, or other fuels and chemicals, from lignocellulosic feedstocks provides an attractive alternative to the feedstocks predominantly used to date such as corn starch, sugar cane, and sugar beets. The production of fermentation products from these latter sources cannot increase much further as most of the farmland suitable for the production of these crops is in use. Cellulose is an abundant natural polymer, so there is an enormous untapped potential for its use as a source for fuels and chemicals. Also, lignocellulosic feedstocks to be used for fuel or chemical production are inexpensive as they have limited use. Another advantage of using these feedstocks for fuel or chemical production is that lignin, which is a byproduct of the cellulose conversion process, can be used as a fuel to power the conversion process, thereby avoiding the use of fossil fuels. Several studies have concluded that, when the entire production and consumption cycle is taken into account, the use of ethanol produced from cellulose generates close to nil greenhouse gases.

The conversion of lignocellulosic feedstocks to a fermentation product is usually carried out with a pretreatment process prior to subsequent steps carried out to liberate glucose from the cellulose contained in the feedstock. Pretreatment makes the feedstock more amenable to subsequent conversion of the cellulose to glucose carried out with cellulase enzymes. The glucose can then be converted to a fermentation product such as ethanol by yeast or bacterium using known methods.

Pretreatment of lignocellulosic feedstocks with dilute sulfuric acid at elevated temperature is commonly described in the literature. Examples of other known pretreatment methods that have been proposed include Organosolv™ pretreatment using an organic solvent and alkali pretreatment using ammonia or other alkali. One chemical pretreatment that has received attention in recent years is pretreatment with sulfur dioxide. Sulfur dioxide is a gas, which when dissolved in water, is referred to as sulfurous acid. Sulfur dioxide and/or sulfurous acid can be added to the lignocellulosic feedstock prior to or during a pretreatment by any of a number of methods, including adding sulfur dioxide gas to the lignocellulosic feedstock or combining dilute sulfurous acid to the lignocellulosic feedstock.

However, there are numerous challenges associated with the use of sulfur dioxide and/or sulfurous acid as a pretreatment chemical. In particular, pretreatment with sulfur dioxide and/or sulfurous acid may produce sulfonated species, such as organic compounds in soluble form, known as sulfonic acids and that these organic compounds may be difficult to handle and dispose of. The production of one or more sulfonic acids and the difficulties with their processing and disposal may impede the commercialization of sulfur dioxide and/or sulfurous acid pretreatment.

SUMMARY

Some embodiments of the invention seek to overcome these disadvantages, or provide one or more alternatives to known processes for producing products from a lignocellulosic feedstock.

As described above, it has been found that the use of sulfurous acid and/or sulfur dioxide in pretreatment may produce sulfonic acid(s). The formation of these compounds presents a number of challenges for the successful commercial implementation of processes comprising pretreating lignocellulosic feedstock with sulfur dioxide and/or sulfurous acid. Because sulfur dioxide and/or sulfurous acid is costly, it is often desirable to recover the chemical and re-use it in pretreatment to off-set the expense of the chemical. However, it is difficult and costly to recover sulfur present in the sulfonic acids produced by pretreatment. Further, sulfonic acid from the pretreatment must be disposed of, but this is a challenge. Anaerobic digestion is often used to treat organic compounds in waste streams, but sulfonic acids such as lignosulfonates or other compounds are not easily digested by microorganisms used in the digestion. Thus, the loss of sulfur present in sulfonic acids and the cost of their disposal can represent significant cost to the process.

The inventors have found that the wet oxidation of one or more sulfonic acids originating from a pretreatment with sulfur dioxide and/or sulfurous acid, followed by anaerobic digestion, can simplify further processing of streams comprising such sulfonic acids. As described herein, wet oxidation of sulfonic acids can improve anaerobic digestion of these compounds and/or allow sulfur dioxide or sulfurous acid to be recovered with greater ease. Wet oxidation may include addition of an oxidant such as air, oxygen, ozone, hydrogen peroxide, chlorine, chlorine dioxide, or other known oxidants in the presence of water.

Thus, according to a first aspect of embodiments of the invention, there is provided a process for producing one or more products from a lignocellulosic feedstock comprising: (i) treating the lignocellulosic feedstock by contacting same with at least sulfur dioxide, sulfurous acid, or a combination thereof to produce a pretreated feedstock composition comprising one or more sulfonic acids; (ii) hydrolyzing the pretreated feedstock with cellulase enzymes to produce glucose; (ii) fermenting the glucose to produce a fermentation product; (iii) providing a process stream comprising the one or more sulfonic acids produced in step (i); (iv) treating the stream comprising the one or more sulfonic acids by a wet oxidation step to produce a stream comprising a sulfate salt and soluble oxidized phenolic compounds; and (v) feeding at least the soluble oxidized phenolic compounds to anaerobic digestion to produce methane.

According to a second aspect of embodiments of the invention, there is provided a process for producing one or more products from a lignocellulosic feedstock comprising: (i) treating the lignocellulosic feedstock by contacting same with at least sulfur dioxide, sulfurous acid, or a combination thereof to produce a pretreated feedstock composition comprising one or more sulfonic acids; (ii) hydrolyzing the pretreated feedstock with cellulase enzymes to produce glucose; (iii) fermenting the glucose to produce an alcohol; (iv) recovering the alcohol produced in step (iii) to produce recovered alcohol and a remaining stream comprising the one or more sulfonic acids; (v) treating the remaining stream comprising the one or more sulfonic acids by a wet oxidation step to produce a stream comprising a sulfate salt and soluble oxidized phenolic compounds; and (vi) feeding at least the soluble oxidized phenolic compounds to anaerobic digestion to produce methane.

According to a third aspect of the invention, there is provided a process for producing one or more products from a lignocellulosic feedstock comprising: (i) treating the lignocellulosic feedstock by contacting same with at least sulfur dioxide, sulfurous acid, or a combination thereof to produce a pretreated feedstock composition comprising one or more sulfonic acids; (ii) providing a process stream comprising the one or more sulfonic acids produced in step (i); (iii) treating the process stream comprising the one or more sulfonic acids by a wet oxidation step to produce a stream comprising a sulfate salt and soluble oxidized phenolic compounds; and (iv) feeding at least the soluble oxidized phenolic compounds to anaerobic digestion to produce methane.

According to a further aspect, there is provided a process for producing one or more products from a lignocellulosic feedstock comprising: (i) treating the lignocellulosic feedstock by contacting same with at least sulfur dioxide, sulfurous acid, or a combination thereof to produce a pretreated feedstock composition comprising one or more sulfonic acids; (ii) providing a process stream comprising the one or more sulfonic acids produced in step (i); (iii) treating the process stream comprising the one or more sulfonic acids by a wet oxidation step to produce a stream comprising soluble oxidized phenolic compounds; and (iv) feeding at least the soluble oxidized phenolic compounds to anaerobic digestion to produce methane.

According to embodiments of any of the foregoing aspects of the invention, the treatment of step (i) comprises combining sulfur dioxide with a slurry comprising the lignocellulosic feedstock. In a further embodiment, the treatment of step (i) comprises combining a solution of sulfurous acid with the lignocellulosic feedstock.

In another embodiment of any of the foregoing aspects of the invention, the anaerobic digestion produces hydrogen sulfide. The hydrogen sulfide may then be treated to produce elemental sulfur or an oxide of sulfur. An acid comprising sulfurous acid, sulfur dioxide, or a combination thereof, may subsequently be recovered from the elemental sulfur or oxide of sulfur. The recovered acid may be used to treat the lignocellulosic feedstock in step (i).

In further embodiments of any of the foregoing aspects of the invention, the one or more sulfonic acids comprise a lignosulfonate, a lignosulfonic acid, or a combination thereof.

According to a further embodiment of any of the foregoing aspects of the invention, the sulfate salt is recovered from the process stream prior to anaerobic digestion.

BRIEF DESCRIPTION OF THE DRAWING

FIG. 1 shows a flow diagram showing pretreating a lignocellulosic feedstock with sulfur dioxide and/or sulfurous acid and subsequently treating a process stream comprising one or more sulfonic acids resulting from the pretreating in a wet oxidation step with oxygen addition to produce a stream comprising at least soluble oxidized phenolic compounds and feeding such stream to an anaerobic digestion to produce a gas comprising methane.

DETAILED DESCRIPTION

Feedstock

In one embodiment, the process utilizes a lignocellulosic feedstock. By the term "lignocellulosic feedstock", it is meant any type of woody or non-woody plant biomass or feedstock derived from plant biomass. The combined content of cellulose, hemicellulose and lignin in the lignocellulosic feedstock is typically greater than 25 wt % (w/w). Sucrose, fructose and starch can be present, but typically in lesser amounts than cellulose and hemicellulose.

Examples of lignocellulosic feedstock are known to those skilled in the art and include: (i) energy crops; (ii) residues, byproducts or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, *miscanthus*, reed canary grass, C3 grasses such as *Arundo donax* or a combination thereof.

Residues, byproducts or waste from the processing of plant biomass in a facility of feedstock derived therefrom include residues remaining after obtaining sugar from plant biomass such as sugar cane bagasse, sugar cane tops and leaves, beet pulp, or residues remaining after removing sugar from Jerusalem artichoke or residues remaining after grain processing, such as corn fiber, corn stover or bran from grains. Agricultural residues include, but are not limited to soybean stover, corn stover, rice straw, sugar cane tops and/or leaves, rice hulls, barley straw, corn cobs, wheat straw, canola straw, oat straw, oat hulls, corn fiber and corn cobs.

Forestry biomass includes recycled wood pulp fiber, sawdust, hardwood, softwood, trimmings and/or slash from logging operations. Pulp and paper waste includes waste from chemical pulping such as black liquor, spent sulfite liquor, sludge and/or fines.

Municipal waste includes post-consumer material or waste from a variety of sources such as domestic, commercial, institutional and/or industrial sources. For example, the term includes refuse from waste collection and/or sewage sludge.

Lignocellulosic feedstock can be a mixture of fibers that originate from different kinds of plant materials, including mixtures of cellulosic and non-cellulosic feedstocks. In addition, the lignocellulosic feedstock may comprise fresh lignocellulosic feedstock, partially dried lignocellulosic feedstock, fully dried lignocellulosic feedstock, or a combination thereof. Moreover, new lignocellulosic feedstock varieties may be produced from any of those listed above by plant breeding or by genetic engineering.

In an embodiment of the invention, the lignocellulosic feedstock is a non-woody lignocellulosic feedstock such as (i) an energy crop, (ii) residues, byproducts or waste from processing of plant biomass or feedstock derived therefrom in a facility, and/or (iii) agricultural residues. In another embodiment of the invention, the lignocellulosic feedstock is straw, stover or an energy crop. As used herein, straw refers to the stem, stalk and/or foliage portion of crops remaining after the removal of starch and/or sugar containing components for consumption. Examples of straw includes, but are not limited to sugar cane tops and/or leaves, oat straw, wheat straw, rye straw, oat straw, rice straw and barley straw. Stover includes the stalk and foliage portion of crops after the removal of starch and/or sugar containing components of plant material for consumption. Examples of stover include but are not limited to soybean stover, sorghum stover and corn stover.

Lignocellulosic feedstocks that have particle sizes of less than about 6 inches may not require size reduction. For feedstocks of larger particle sizes, the feedstock may be subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. In one embodiment, at least 90% by volume of the particles produced from the size reduction may have a length less than between about 1/16 and about 6 inches. Suitable equipment for the particle size reduction is a hammer mill, a refiner or a roll press as disclosed in WO 2006/026863.

Optionally, before, during or subsequent to size reduction, the feedstock can be slurried in liquid, which allows the feedstock to be pumped. The desired weight ratio of water to dry lignocellulosic feedstock solids in the slurry is determined by factors such as pumpability, pipe-line requirements, and other practical considerations. However, it should be understood that the feedstock need not be slurried, but rather could be pretreated without any prior addition of liquid.

Examples of the undissolved solids concentration of the lignocellulosic feedstock are between 20% and 100 wt % or between about 20 wt % and about 80 wt % (w/w).

The feedstock may be heated with steam during or prior to pretreatment. Without being limiting, one method to carry this out is to use low pressure steam to partially heat the feedstock. Other means may be employed to heat the feedstock, such as commercially available mixing devices designed for introducing steam and optionally acid through spray nozzles.

Pretreatment

The lignocellulosic feedstock is contacted with at least sulfur dioxide, sulfurous acid, or a combination thereof. That is, the feedstock may be contacted with sulfur dioxide gas and/or a solution comprising sulfurous acid. Sulfurous acid may be produced upon the addition of sulfur dioxide to an aqueous solution. The sulfur dioxide may be added to a feedstock in wet form, such as a slurry, a feedstock that is in dry form, or a feedstock that has been subjected to a steam treatment. The feedstock may also be contacted with an aqueous solution comprising sulfurous acid prior to pretreatment. For example, the feedstock may be soaked in an aqueous solution comprising sulfurous acid and subsequently subjected to elevated temperature to pretreat the feedstock. The pretreatment may additionally comprise contacting the feedstock with other acids or chemicals besides sulfurous acid if desired.

The pretreatment produces a pretreated feedstock composition comprising one or more sulfonic acids. As would be appreciated by those of skill in the art, the sulfonic acid species present in solution depends on the pH. Thus, the term sulfonic acid(s) encompasses sulfonic acid species, sulfonate species, or both sulfonic acid and sulfonate species. Non-limiting examples of sulfonic acids produced by the pretreatment include lignosulfonates (e.g., sulfonated compounds of a relatively high molecular weight) and/or lower molecular weight sulfonic acids. In one embodiment of the invention, the pretreatment produces at least a lignosulfonate. Further, the pretreatment may produce soluble phenolic compounds, such as soluble lignin, low molecular weight phenolics, and/or one or more salts such as sulfite salts.

The pretreatment is generally conducted so as to disrupt the fiber structure of the lignocellulosic feedstock and increase its surface area to make it accessible to cellulase enzymes. The pretreatment may be performed so that a certain degree of xylan hydrolysis is achieved and only a small amount of conversion of cellulose to glucose occurs.

The pretreatment may be conducted to achieve a pH between about 1.0 and about 3.0. The pH is measured at any stage during the time course of the pretreatment and is measured at ambient temperature.

Without being limiting, the pretreatment may be carried out at a maximum temperature of about 170° C. to about 230° C. However, in practice, there will be a time delay in the pretreatment process before the feedstock reaches this temperature range. The above temperatures correspond to those values reached after sufficient application of heat to reach a temperature within this range. The time that the feedstock is held at this temperature may be about 10 seconds to about 30 minutes, or any range therebetween.

According to one embodiment of the invention, the soluble components of the pretreated feedstock composition are separated from the solids to produce an aqueous stream comprising sugars such as xylose, glucose, arabinose mannose and/or galactose and one or more sulfonic acids. The sulfonic acids include soluble compounds originating from lignin and its reaction with sulfur dioxide and/or sulfurous acid. These include sulfonic acids such as lignosulfonates or lower molecular weight sulfonic acids. Further, the stream may comprise soluble phenolic compounds, such as soluble lignin, low molecular weight phenolics and/or one or more salts such as sulfite salts.

This separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation using known methods such as centrifugation, microfiltration, plate and frame filtration, crossflow filtration, pressure filtration, vacuum filtration, and the like. Optionally, a washing step may be incorporated into the solids-liquids separation. The separated solids, which contain cellulose and lignin, for example both native and sulfonated, may subsequently be sent to enzymatic hydrolysis with cellulase enzymes in order to convert the cellulose to glucose. The enzymatic hydrolysis of cellulose using cellulase enzymes is described in more detail below.

Enzymatic Hydrolysis

The cellulose is hydrolyzed to glucose in a step that uses cellulase enzymes. Prior to the addition of enzyme, the pH of the pretreated feedstock composition is adjusted to a value that is suitable for the enzymatic hydrolysis reaction. Typically, this involves the addition of alkali to a pH of between about 4 to about 6, which is the optimal pH range for cellulases, although the pH can be higher if alkalophilic cellulases are used.

The enzymatic hydrolysis of the cellulose to soluble sugars can be carried out with any type of cellulase enzymes suitable for such purpose and effective at the pH and other conditions utilized, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens* (see Lynd et al., 2002, Microbiology and Molecular Biology Reviews, 66(3):506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12).

In addition to CBH, EG and beta-glucosidase, there are several accessory enzymes that aid in the enzymatic digestion of cellulose (see WO 2009/026722 (Scott), which is incorporated herein by reference and Harris et al., 2010, Biochemistry, 49:3305-3316). These include EGIV, also known as glycoside hydrolase 61, swollenin, expansin, lucinen and cellulose-induced protein (Cip). Glucose can be enzymatically converted to the dimers gentiobiose, sophorose, laminaribiose and others by beta-glucosidase via transglycosylation reactions.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268). An example of a cellulase dosage is about 10 to 20 FPU per gram cellulose.

The dosage may also be measured in units of milligrams of protein per gram of cellulose. An example of a dose in these units is 2 to 20 mg protein per gram cellulose.

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used in the practice of this invention. It is also contemplated that the β-glucosidase enzyme may be modified to include a cellulose binding domain, thereby allowing this enzyme to bind to cellulose.

Alkali can be added to the pretreated feedstock after it is cooled, before cooling, or at points both before and after cooling. The point of alkali addition can coincide with the cellulase enzyme addition, or the addition point can be upstream or downstream of the location of the enzyme addition. If the enzyme is added upstream of the alkali addition point, the contact time of the enzyme at the lower pH of the pretreated feedstock would typically be minimized to avoid enzyme inactivation. The alkali may be added prior to enzyme addition or simultaneously therewith.

In one embodiment, the temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes. The duration of the enzymatic hydrolysis may be from 12 to 200 hours or any range therebetween.

The enzymatic hydrolysis and fermentation may be conducted in separate vessels so that each biological reaction can occur at its respective optimal temperature. However, the hydrolysis may be conducted simultaneously with fermentation in a simultaneous saccharification and fermentation (SSF). SSF is typically carried out at temperatures of 35-38° C., which is a compromise between the 50° C. optimum for cellulase and the 28° C. optimum for yeast.

Fermentation

Fermentation of glucose resulting from the hydrolysis may produce one or more of the fermentation products selected from an alcohol, a sugar alcohol, an organic acid, and a combination thereof.

The fermentation is typically conducted at a pH between about 4.0 and about 6.0, or between about 4.5 and about 6.0. To attain the foregoing pH range for fermentation, it may be necessary to add alkali to the stream comprising glucose.

In one embodiment of the invention, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (e.g., U.S. Pat. Nos. 5,789,210, 5,866,382, 6,582,944 and 7,527,927 and European Patent No. 450530) or (b) fungal or bacterial xylose isomerase (XI) gene (e.g., U.S. Pat. Nos. 6,475,768 and 7,622,284). Examples of yeasts that have been genetically modified to ferment L-arabinose include, but are not limited to, recombinant *Saccharomyces* strains into which genes from either fungal (e.g., U.S. Pat. No. 7,527,951) or bacterial (e.g., WO 2008/041840) arabinose metabolic pathways have been inserted.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation product is recovered, meaning that it is concentrated and/or purified from a fermented solution. A remaining stream contains components besides the fermentation product remaining after the recovery. Non-limiting examples of such components include inorganic salts, unfermented sugars, and organic salts.

If ethanol or butanol is the fermentation product, the recovery is carried out by distillation, typically with further concentration by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is typically operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

A still bottoms stream remaining after ethanol distillation, which may contain solids, is withdrawn from the bottom of one or more of the column(s) of the distillation unit. This still bottoms stream will contain inorganic salts, unfermented sugars, and organic salts.

When the alcohol has a higher boiling point than water, such as butanol, the distillation is run to remove the water and other volatile compounds from the alcohol. The water vapor exits the top of the distillation column and is known as the "overhead stream".

Wet Oxidation

The wet oxidation may be conducted on any process stream comprising the one or more sulfonic acids, for example sulfonated lignin, resulting from treating the lignocellulosic feedstock by contacting it with at least sulfur dioxide, sulfurous acid, or a combination thereof. An example of a process stream that can be subjected to wet oxidation is a stream remaining after recovery of the fermentation product, such as, for example, a still bottoms stream. An example of another stream that can be subjected to the wet oxidation step is an aqueous stream comprising one or more soluble components separated from the pretreated feedstock as described previously.

Optionally both streams may be subjected to the wet oxidation step, in which case the steams may be combined and fed to the wet oxidation or fed separately to the wet oxidation. It should be understood that other streams comprising one or more sulfonic acids may be fed to the wet oxidation as well.

By the term "wet oxidation", it is meant oxidizing a process stream under any suitable conditions in which water is present. The process stream subjected to wet oxidation may contain any amount of water. In one embodiment, the process stream contains at least 50% by weight water (w/w). In one embodiment, the process stream contains or at least 80% by weight water (w/w).

In the wet oxidation step, the oxidant contacted with the process stream comprising one or more sulfonic acids can be any suitable oxidant. Examples of oxidants are air, oxygen, ozone, hydrogen peroxide, chlorine, chlorine dioxide or other known oxidants. In one embodiment of the invention, the oxidant is air or oxygen. Typically, an oxygen stream is purified from air.

The oxidant may be added at a concentration corresponding to 30% to 150% of the chemical oxygen demand (COD) of the process stream comprising one or more sulfonic acids. As would be appreciated by those of skill in the art, lower concentrations of oxidant during the wet oxidation will result in a less complete oxidation than higher concentrations. Thus, the concentration of oxidant added during the wet oxidation step will vary depending on the degree of wet oxidation desired.

The wet oxidation conditions can be readily selected by those of skill in the art to achieve a suitable level of oxidation and may depend on the particular oxidant that is utilized. With air or oxygen, the treatment may be between about 140 and about 320° C. or between about 140 and about 200° C. The pH may range from about 2 to about 12. The pH can be adjusted by adding acid or alkali to the process stream or during the wet oxidation step. Without being limiting, alkali may also be added to the process stream to adjust its pH prior to wet oxidation. The duration of the wet oxidation with air or oxygen includes any suitable time period and may range from 10 minutes to 2 hours. If ozone is used as the oxidant the temperature may range from 0° C. to about 60° C. and the treatment duration may be between about 5 and about 30 minutes. It should be appreciated that the foregoing treatment conditions are non-limiting and can be varied as required to obtain a suitable level of wet oxidation.

The wet oxidation can be conducted in batch or continuous mode. An example of a known commercially available unit for conducting the wet oxidation step is a Zimpro® wet oxidation unit available from Siemens.

The wet oxidation step produces an oxidant treated stream comprising one or more soluble, oxidized phenolics. The molecular weight of the soluble oxidized phenolics, for example oxidized lignin, in the oxidant treated stream may be lower than prior to wet oxidation. Furthermore, sulfur in solution after wet oxidation may be in the form of sulfuric acid and/or sulfate salts, including bisulfate salts. The molecular weight of other components in the oxidant treated stream, such as insoluble oxidized sulfonated lignin may also be lower than prior to wet oxidation.

Insoluble solids may be removed from the oxidant treated stream by any known methodology, such as a solids-liquid separation. The solids-liquid separation produces a process stream comprising insoluble solids and an aqueous stream.

A non-limiting example of a suitable solids-liquid separation for removing insoluble solids is filtration.

The aqueous stream comprises soluble sulfonic acid(s) as well as sulfuric acid and/or sulfates. Sulfuric acid and/or sulfate salts may optionally be removed and recovered from the aqueous stream by known techniques such as extraction, anion exchange, or other suitable known processes. The aqueous stream comprising at least soluble oxidized phenolic compounds is subsequently subjected to anaerobic digestion.

Anaerobic Digestion

Anaerobic digestion is used to treat the aqueous stream comprising at least soluble oxidized phenolic compounds. As used herein, anaerobic digestion encompasses any method for microbially digesting components in the aqueous stream. Generally, the anaerobic digestion is conducted with microorganisms under low oxygen conditions, or in the absence of oxygen, to produce a gas comprising at least methane or "biomethane". The gas may comprise other components in addition to methane, such as carbon dioxide and water and optionally hydrogen sulfide, if sulfur has not been removed. The gas comprising methane and optionally other components is also referred to as "biogas".

The digestion may be conducted in an anaerobic digester, which is a tank, or other contained volume, such as a covered lagoon, designed to facilitate the breakdown of organic material in the aqueous stream by microorganisms under anaerobic or low oxygen conditions. The anaerobic digestion may be carried out in one or multiple anaerobic digesters connected in series, parallel or a combination thereof. Thus, the anaerobic digester may be one or a plurality of fluidly connected digesters.

An anaerobic digester utilized in accordance with embodiments of the invention may be designed and/or operated in a number of configurations including batch or continuous systems. The conditions utilized may depend on a number of factors that can be readily selected by those of skill in the art. These may include consideration of the nature of the organic material in the aqueous stream to be treated and/or the level of treatment desired. Mesophilic or thermophilic temperature ranges may be selected. Low, medium or high rates may be selected for the digestion. The rate refers to the reduction (or digestion) of chemical oxygen demand (COD) per unit of volume to the unit, which is a rate measurement based on the removal of organic compounds present in the feed to the digester. The anaerobic digester may be adapted for handling or concentrating microbes. For example, the digester may utilize membranes, packing, settling and recycling.

The microorganisms typically produce biogas comprising at least methane and carbon dioxide from the organics. The soluble oxidized phenolic compounds may be biologically broken down during the anaerobic digestion to produce methane.

The biogas produced by the digestion may be purified by known techniques. Impurities in the gas comprising methane may include, without limitation, carbon dioxide, water, siloxanes, oxygen, nitrogen and/or halogenated compounds, and hydrogen sulfide. The impurities in the biogas can be removed by any suitable method, or combination of methods, to yield at least partially purified methane. Non-limiting examples for removing impurities include scrubbing, pressure swing adsorption and/or membrane separation. For example, between 20% and 100% by weight of the carbon dioxide may be removed by weight from the gas comprising methane. The methane may then be used as a heating fuel, transportation fuel or to produce electricity.

When the aqueous stream sent to anaerobic digestion comprises sulfur, it may be converted to hydrogen sulfide in the digester. Such conversion may be carried out by sulfate and/or sulfite reducing bacteria present during the anaerobic digestion. The resultant hydrogen sulfide produced from anaerobic digestion may subsequently be treated to produce element sulfur or oxides of sulfur, such as sulfur dioxide. An acid comprising sulfurous acid, sulfur dioxide, or a combination thereof may be recovered from the elemental sulfur or oxides of sulfur. This acid may then be used in the pretreatment. Thus, the sulfur originating from one or more sulfonic acids can be converted to sulfurous acid and/or sulfur dioxide that can be re-used in the pretreatment. This in turn reduces pretreatment chemical usage, which can potentially reduce the cost of the pretreatment.

DESCRIPTION OF AN EMBODIMENT OF THE INVENTION

An embodiment of the invention is depicted in the flowsheet described in FIG. 1. As shown in FIG. 1, an incoming lignocellulosic feedstock slurry 2 is treated with a stream of gaseous sulfur dioxide 4. Upon addition of the stream of gaseous sulfur dioxide 4 to the lignocellulosic feedstock slurry 2, sulfurous acid is produced, which is in contact with the feedstock during pretreatment 6. The pretreatment 6 is conducted at a pH of between 1.0 and 2.5 and a temperature between 170 and 230° C. and produces a pretreated feedstock slurry 8 comprising sugars selected from xylose, glucose, arabinose, mannose and galactose, soluble products from the reaction of lignin with sulfur dioxide and/or sulfurous acid including sulfonic acids, sulfite salts, and soluble native lignin, and unhydrolyzed cellulose and lignin (native and sulfonated). The pretreated feedstock slurry 8 may be subsequently subjected to a separation step. This separation step may be carried out by washing the pretreated feedstock slurry 8 in a washing step 10 to produce a wash stream 12. A solids stream 13 comprising the unhydrolyzed, pretreated feedstock is cooled to 40 to 60° C. and alkali is added to achieve a pH between 4 and 6. The solids stream 13 is then subjected to hydrolysis 14 with cellulase enzymes. The enzymatic hydrolysis 14 with cellulase enzymes is conducted by adding cellulase enzymes at a dosage of 2 to 20 mg protein per gram of cellulose for 12 to 200 hours. The cellulose hydrolysis 14 produces a hydrolyzate stream 16 comprising glucose. The hydrolyzate stream 16 resulting from the hydrolysis 14 is fed to a fermentation 18 to produce ethanol using *Saccharomyces cerevisiae* yeast under conventional conditions. The fermentation 18 produces a fermented solution 20 comprising the ethanol and carbon dioxide stream 22. The fermented solution 20 is fed to distillation 22 in which ethanol is recovered. Distillation 22 produces a concentrated ethanol stream 23, which may be further concentrated by molecular sieves or other concentration methods (not shown). The distillation 22 also produces a still bottoms stream 24 that remains after distillation 22. Optionally, an alkali stream 26 is added to the still bottoms stream 24 to increase its pH. The still bottoms stream 24 is then subjected to a wet oxidation 28. The wash stream 12 comprising sugar and lignosulfonates produced during optional washing step 10 may also be added to the wet oxidation 28.

The wet oxidation 28 comprises the addition of an oxygen-containing stream 30. Wet oxidation of the still bottoms stream 24 and the wash stream 12 with oxygen from oxygen-containing stream 30 is conducted under conditions to solubilise and oxidize the majority of the lignin and produces an oxidant treated stream 32. The molecular weight of the soluble, oxidized lignin in the oxidant treated stream 32 is significantly lower than prior to the wet oxidation 28. Additionally, the sulfur in solution after wet oxidation 28 is in the form of sulfuric acid and/or sulfate salts.

The oxidant treated stream 32 is subsequently fed to a filtering step which produces a solids stream 36 and an aqueous stream 38. The aqueous stream 38 comprises soluble phenolic compounds and also sulfates and/or sulfuric acid. Sulfuric acid and/or sulfate salts optionally may be removed from the aqueous stream by a sulfate removal step 40 such as by extraction, anion exchange or other suitable known processes. An aqueous stream 42 comprising at least soluble phenolic compounds is subsequently subjected to anaerobic digestion 44. In the anaerobic digestion 44, the aqueous stream is digested with microorganisms. A gas stream 46 comprising at least methane and carbon dioxide is removed from the digestion 44. If sulfate removal 40 is not conducted, the gas withdrawn from the digestion 44 will additionally comprise hydrogen sulfide.

The resultant hydrogen sulfide produced from anaerobic digestion may subsequently be treated to produce element sulfur or oxides of sulfur, such as sulfur dioxide. An acid comprising sulfurous acid, sulfur dioxide or a combination thereof may be recovered from the elemental sulfur or oxides of sulfur. This acid or acids may then be used in the pretreatment 6 to reduce chemical usage.

As discussed above, the sulfonic acids (e.g., lignosulfonates) produced during pretreatment may impede the commercialization of sulfur dioxide and/or sulfurous acid pretreatment as a result of the difficulties associated with their processing and/or disposal. Providing a wet oxidation step upstream from anaerobic digestion, advantageously may depolymerize some of the lignosulfonates to provide soluble oxidized phenolic compounds and/or sulfate salts. Advantageously, the wet oxidation step makes the anaerobic digestion step more efficient and effective. For example, the soluble oxidized phenolic compounds may provide more methane than the sulfonic acids fed into the wet oxidation. Further advantageously, the wet oxidation facilitates the recovery of sulfur. For example, the sulfur in the sulfur salts provided by the wet oxidation and/or the hydrogen sulfide provided by the anaerobic digestion may be easier to isolate and/or process.

The present invention has been described with regard to one or more embodiments. However, it will be apparent to persons skilled in the art that a number of variations and modifications can be made without departing from the scope of the invention as defined in the claims.

The invention claimed is:

1. A process for producing one or more products from a lignocellulosic feedstock comprising:
   (i) treating the lignocellulosic feedstock by contacting same with at least sulfur dioxide, sulfurous acid, or a combination thereof to produce a pretreated feedstock composition comprising one or more sulfonic acids;
   (ii) hydrolyzing the pretreated feedstock with cellulase enzymes to produce glucose;
   (iii) fermenting the glucose to produce a fermentation product;
   (iv) providing a process stream comprising the one or more sulfonic acids produced in step (i);
   (v) treating the process stream comprising the one or more sulfonic acids by a wet oxidation step to produce a stream comprising a sulfate salt and soluble oxidized phenolic compounds; and
   (vi) feeding at least the soluble oxidized phenolic compounds to anaerobic digestion to produce methane.

2. A process for producing one or more products from a lignocellulosic feedstock comprising:
   (i) treating the lignocellulosic feedstock by contacting same with at least sulfur dioxide, sulfurous acid, or a combination thereof to produce a pretreated feedstock composition comprising one or more sulfonic acids;
   (ii) hydrolyzing the pretreated feedstock with cellulase enzymes to produce glucose;
   (iii) fermenting the glucose to produce an alcohol;
   (iv) recovering the alcohol produced in step (iii) to produce recovered alcohol and a remaining stream comprising the one or more sulfonic acids;
   (v) treating the remaining stream comprising the one or more sulfonic acids by a wet oxidation step to produce a stream comprising a sulfate salt and soluble oxidized phenolic compounds; and
   (vi) feeding at least the soluble oxidized phenolic compounds to anaerobic digestion to produce methane.

3. A process for producing one or more products from a lignocellulosic feedstock comprising:
   (i) treating the lignocellulosic feedstock by contacting same with at least sulfur dioxide, sulfurous acid, or a combination thereof to produce a pretreated feedstock composition comprising one or more sulfonic acids;
   (ii) providing a process stream comprising the one or more sulfonic acids produced in step (i);
   (iii) treating the process stream comprising the one or more sulfonic acids by a wet oxidation step to produce a stream comprising a sulfate salt and soluble oxidized phenolic compounds; and
   (iv) feeding at least the soluble oxidized phenolic compounds to anaerobic digestion to produce methane.

4. The process of claim 1, wherein the treatment of step (i) comprises combining gaseous sulfur dioxide with a slurry comprising the lignocellulosic feedstock.

5. The process of claim 1, wherein the treatment of step (i) comprises combining a solution of sulfurous acid with the lignocellulosic feedstock.

6. The process of claim 1, wherein the anaerobic digestion produces hydrogen sulfide.

7. The process of claim 6, wherein the process further comprises
   (a) treating the hydrogen sulfide to produce elemental sulfur or an oxide of sulfur;
   (b) recovering an acid comprising sulfurous acid, sulfur dioxide or a combination thereof from the elemental sulfur or oxide of sulfur; and
   (c) using the acid recovered in step (b) in step (i) of treating the lignocellulosic feedstock.

8. The process of claim 1, further comprising recovering the fermentation product to produce a recovered product and a remaining stream comprising one or more sulfonic acids.

9. The process of claim 8, wherein the remaining stream is treated by the wet oxidation.

10. The process of claim 1, wherein the wet oxidation step comprises the addition of air or oxygen.

11. The process of claim 1, wherein the one or more sulfonic acids comprise a lignosulfonate, a lignosulfonic acid, or a combination thereof.

12. The process of claim 1, wherein the sulfate salt is recovered from the process stream prior to anaerobic digestion.

13. A process for producing one or more products from a lignocellulosic feedstock comprising:
   (i) treating the lignocellulosic feedstock by contacting same with at least sulfur dioxide, sulfurous acid, or a combination thereof to produce a pretreated feedstock composition comprising one or more sulfonic acids;
   (ii) providing a process stream comprising the one or more sulfonic acids produced in step (i);
   (iii) treating the process stream comprising the one or more sulfonic acids by a wet oxidation step to produce a stream comprising soluble oxidized phenolic compounds; and
   (iv) feeding at least the soluble oxidized phenolic compounds to anaerobic digestion to produce methane.

* * * * *